United States Patent [19]

Collins

[11] Patent Number: 4,772,465
[45] Date of Patent: Sep. 20, 1988

[54] METHOD OF TREATING POLYMICROBIAL BURN WOUND SEPSIS WITH A COMBINATION THERAPY OF CIPROFLOXACIN AND PSEUDOMONAS IMMUNE GLOBULIN

[75] Inventor: Michael S. Collins, Pinole, Calif.

[73] Assignee: Miles Laboratories, Inc., Elkhart, Ind.

[21] Appl. No.: 923,360

[22] Filed: Oct. 27, 1986

[51] Int. Cl.$^4$ .................... A61K 39/40; A61K 39/395
[52] U.S. Cl. ..................................... 424/87; 424/85.8; 530/387; 435/874
[58] Field of Search .................... 424/85, 87; 530/387; 435/874

[56] References Cited

U.S. PATENT DOCUMENTS

| | | | |
|---|---|---|---|
| 4,120,950 | 10/1978 | Homma | 424/87 X |
| 4,157,389 | 6/1979 | Homma et al. | 424/87 X |
| 4,482,483 | 11/1984 | Curry et al. | 424/87 X |
| 4,587,121 | 5/1986 | Collins et al. | 424/87 |
| 4,677,070 | 6/1987 | Larrick et al. | 424/87 X |

OTHER PUBLICATIONS

Inf. Immun. 39:1072–1079 (1983), Cryz, Jr. et al.
J. Infect. Dis. 147, 1090–1098 (1983), Pollack.
J. of Trauma, 23:530–534 (1983), Collins et al.
Am. J. Med. 76 (3A), 168–174 (1984), Collins et al.
Antimicrob. Agents Chemother. 26, 757–761 (1984), Brumfitt et al.
Antimicrob. Agents Chemother. 26:1–4 (1984), Schiff et al.
Antimicrob. Agents Chemother. 25, 319+326 (1984), Chin et al.
Antimicrob. Agents Chemother. 25, 331–335 (1984), Elipoulos et al.

*Primary Examiner*—Howard E. Shain
*Attorney, Agent, or Firm*—James A. Giblin; Pamela A. Simonton

[57] ABSTRACT

A method for increasing the survival rate in hypercatabolic mammals following the onset of burn wound sepsis. The method comprises orally administering to the mammal, sufficient doses of ciprofloxacin to attain high concentrations in extra vascular fluid, and parenterally administering to the mammal, Pseudomonas immune globulin. The combination therapy of treating Pseudomonas burn wound sepsis with ciprofloxacin and Pseudomonas immune globulin results in a higher rate of survival than the treatment utilizing a single agent. This suggests a synergistic interaction between the two agents in the therapy of polymicrobial burn wound sepsis.

6 Claims, No Drawings

METHOD OF TREATING POLYMICROBIAL BURN WOUND SEPSIS WITH A COMBINATION THERAPY OF CIPROFLOXACIN AND PSEUDOMONAS IMMUNE GLOBULIN

BACKGROUND OF THE INVENTION

1. Field:

This disclosure is concerned generally with therapy for Pseudomonas burn wound sepsis (PBWS) and specifically with the use of Pseudomonas immune globulin and ciprofloxacin as a combination therapy.

2. Prior Art:

Although infection with Pseudomonas aeruginosa (P. aeruginosa) is not common among the general population, P. aeruginosa infection is encountered very frequently in certain susceptible groups of patients. Burn victims and immunosuppressed cancer patients have been identified as having an unusually high risk of acquiring severe, and sometimes fatal, P. aeruginosa infection. P. aeruginosa infections are usually acquired during a hospital stay, not at home.

Bacterial infection is the leading cause of death among burn patients. (Monafo, W. W., 1979. An overview of infection control. J. Trauma 19 (Suppl): 879–80). Pseudomonas aeruginosa continues to be a major pathogen in burn infection. (McManus, W. F., C. W. Goodwin, A. D. Mason, Jr., and B. A. Pruitt. 1981. Burn Wound Infection. J. Trauma 21: 753–756). Numerous studies have demonstrated that pooled human IgG concentrates are protective in experimental Pseudomonas burn wound infection. For example, see Collins, M. S., and R. E. Roby. 1983. Anti-Pseudomonas aeruginosa activity of an antravenous human IgG preparation in burned mice. J. Trauma 23: 530–534. The development of IgG concentrates for intravenous infusion (IGIV) permits twice weekly infusion of 500 mg IgG/kg into burn patients without undesirable side effects. (Shirani, K. Z., G. M. Vaughan, A. T. McManus, B. W. Amy, W. F. McManus, B. A. Pruitt, and A. D. Mason. 1984. Replacement therapy with modified immunoglobulin G in burn patients: preliminary kinetic studies. Am. J. Med. 76(3A): 175–180). Our laboratory recently described an IGIV preparation enriched in antibodies to lipopolysaccharide (LPS) antigens of P. aeruginosa (PS-IGIV). PS-IGIV is prepared from plasma of donors that have naturally high levels of IgG antibody to LPS. (Collins, M. S., and R. E. Roby. 1984. Protective activity of an intravenous immune globulin (human) enriched in antibody against lipopolysaccharide antigens of Pseudomonas aeruginosa. Am. J. Med. 76(3A) 168–174). This strategy circumvents the need to immunize donors with experimental and potentially toxic vaccines. PS-IGIV is several-fold more potent than conventional IGIV in prophylaxis of experimental burn wound sepsis. In the therapy of established infection, combinations of PS-IGIV and tobramycin afford significantly greater survival in animal models than single agent therapy.

Nearly three decades ago it was reported that pooled human IgG is protective against experimental P. aeruginosa infection in normal and burned animals. (Fisher, M. W., and M. C. Manning. 1958. Studies on the immunotherapy of bacterial infections. I. The comparative effectiveness of human gammaglobulin against various bacterial species in mice. J. Immunol. 81: 29–31; and Rosenthal, S. M., R. C. Millican and J. Rust. 1957. A factor in human gamma-globulin preparations active against Pseudomonas aeruginosa infections. Proc. Soc. Exp. Biol. Med. 94: 214–217). Attempts in the 1960's to treat Pseudomonas infection with immune globulin were not very successful in part because of the limited amount of IgG that could be delivered by intramuscular injection of IgG concentrates. (Kefalides, N. A., J. A. Arana, A. Bazan, M. Bocanegra, P. Stastny, N. Velarde, and S. M. Rosenthal. 1962. Role of infection in mortality from severe burns: evaluation of plasma, gamma-globulin, albumin and saline solution therapy in a group of Peruvian Children, N. Engl. J. Med. 267: 317–323 and Stone, H. H., C. D. Graber, J. D. Martin, and L. Kolb. 1965. Evaluation of gamma globulin for prophylaxis against burn sepsis. Surgery 58: 810–814).

Passive protection studies using sera of animals immunized with LPS provide proof that IgG antibody to LPS is highly protective against P. aeruginosa in experimental infections. (Cryz, S. J., E. Furer, and R. Germanier. 1983. Protection against P. aeruginosa infection in a murine burn wound sepsis model by passive transfer of antitoxin A, antielastase and antilipopolysaccharide. Infect. Immun. 39: 1072–1079). The protective activity of IGIV in experimental P. aeruginosa infection prompted this laboratory to consider that an IGIV enriched in antibodies to LPS might be more protective than IGIV prepared from plasma of random donors. (Pollack, M. 1983. Antibody activity against P. aeruginosa in immune globulins prepared for intravenous use in humans. J. Infect. Dis. 147: 1090–1098). Accordingly, several thousand donors were tested by ELISA for IgG titers to LPS antigens of the seven Fisher-Devlin-Gnabasik (FDG) immunotypes of P. aeruginosa.

Approximately 5% of plasma donors had antibody titers $\geq 1:1,600$ against FDG 1, 2, 4 and 6 LPS. Several hundred liters of plasma were obtained from ELISA tested donors, and PS-IGIV was produced. PS-IGIV is enriched from 4.84 to 11.72-fold in antibody to FDG 1, 2, 4 and 6 LPS (Table 1). Although not of intentional design, PS-IGIV is also enriched several-fold in IgG to FDG 3, 5 and 7. The present study indicates that PS-IGIV prophylaxis was protective in burned mice against all 18 clinical isolates examined. It should be noted that these 18 isolates were not preliminarily screened for sensitivity to IgG prophylaxis. Against 16 of these strains, the mean protective dose ($PD_{50}$) of PS-IGIV was $\leq 100$ mg IgG/kg body weight. PS-IGIV tended to be more protective against strains expressing FDG LPS antigens. Approximately 90% of P. aeruginosa strains isolated from serious infections fall within the FDG immunotype system (Fisher, M. W., H. B. Devlin and F. J. Gnabasik. 1969. New immunotype schema for P. aeruginosa based on protective antigens. J. Bacteriol. 98: 835–836).

Pseudomonas Immune Globulin, Intravenous (PS-IGIV) is currently in clinical trials in the US and Europe. PS-IGIV is prepared from plasma of donors that have naturally high levels of IgG antibody to lipopolysaccharide antigens of P. aeruginosa, as set forth in U. S. Pat. No. 4,587,121. It contains 5% IgG in 10% maltose and is prepared for intravenous infusion by a low pH process. The prophylactic activity of PS-IGIV is a burned mouse model was evaluated against 18 clinical isolates of P. aeruginosa representing 17 distinct International Antigenic Typing System serotypes. In burned mice challenged with approximately 10 to 100 mean lethal doses ($LD_{50}$) the $PD_{50}$ against the 18 strains ranged from less than 56 to 252 mg IgG/kg. In part, PS-IGIV protection may have resulted from neutralization of exotoxin A. In PS-IGIV treated mice challenged with 4 $LD_{50}$ of exotoxin A, serum levels of aspartate and alanine aminotransferase were several-fold lower than those of mice treated with conventional IgG concentrates.

The present invention is not limited to the parenteral administration of PS-IGIV, but includes other immune globulin preparations, including but not limited to intramuscular preparations, intravenous preparations and hyperimmune globulins. Other immune globulin preparations, such as IgM preparations for intravenous and intramuscular administration may be effective, in combination therapy with quinoline derivatives such as ciprofloxacin in the treatment of burn wound sepsis.

Ciprofloxacin is a recently developed quinoline carboxylic acid derivative that is well absorbed when given orally and attains high concentrations in extravascular fluid. Ciprofloxacin is highly active against P. aeruginosa in vitro (Chin, N., and H. C. Nev. 1984. Ciprofloxacin, a quinoline carboxylic acid compound active against aerobic and anaerobic bacteria. Antimicrob. Agents Chemother. 25: 319–326 and Eliopoulos, G. M., A. Gardella, and R. C. Moellering, Jr. 1984. In vitro activity of ciprofloxacin, a new carboxyquinoline antimicrobial agent. Antimicrob. Agents Chemother. 25: 331–335). Ciprofloxacin is active against P. aeruginosa pneumonia in guinea pigs (Schiff, J. B., G. J. Small, and J. E. Pennington. 1984. Comparative activities of ciprofloxacin, ticarcillin and tobramycin against experimental P. aeruginosa pneumonia. Antimicrob. Agents Chemother. 26: 1–4). In humans ciprofloxacin has been given orally at dosages ranging from 5.2 to 8.7 mg/kg/dose twice daily for seven days. This oral regimen appeared safe and led to serum levels of the drug that exceeded the in vitro MIC of ciprofloxacin against a large number of clinical strains of P. aeruginosa (Brumfitt, W., I. Franklin, O. Grady, J. M. T. Hamilton-Miller, and A. Iliffee. 1984. Changes in the pharmacokinetics of ciprofloxacin and fecal flora during administration of a 7-day course to human volunteers. Antimicrob. Agents Chemother. 26: 757–761).

P. aeruginosa is resistant to penicillin G. A combination of a P. aeruginosa specific penicillin and an aminoglycoside is the usual therapy for P. aeruginosa sepsis and has greatly contributed to the survival of patients, particularly leukemics. The management of P. aeruginosa in burn patients is also dependent upon topical antimicrobial therapy. But, the rapid emergence of antibiotic resistance by P. aeruginosa and the relatively high toxicity of potent anti-Pseudomonas agents such as aminoglycosides provide impetus to the continuing development and clinical evaluation of new therapeutic agents.

In addition to P. aeruginosa, a weakly virulent strain of Staphylococcus aureus ($LD_{50} > 10^8$ cfu) has been found to greatly enhance the virulence of several strains of P. aeruginosa in experimental burn wound infection. Polymicrobial burn wound sepsis induced by approximately 100 cfu of P. aeruginosa and 50 cfu of S. aureus was found to be a lethal infection in challenged mice.

SUMMARY OF THE INVENTION

I have found that it is possible to increase the survival rate in a hypercatabolic mammal by orally administering to the mammals dosages of ciprofloxacin and parenterally administering to the same mammals dosages of Pseudomonas immune globulin. It has been found that Pseudomonas immune globulin enhances the effect of ciprofloxacin therapy of established Pseudomonas burn wound sepsis. The survival rate of mammals following treatment of the combination therapy was greater than the survival rate of the sum of mammals receiving a sole agent. This unexpected result supports the observation that Pseudomonas immune globulin enhances the potency or effectiveness of ciprofloxacin.

DETAILED DESCRIPTION OF THE INVENTION

As discussed below I assessed in a burned animal model the prophylactic activity of PS-IGIV against 18 clinical isolates of P. aeruginosa that represent 17 distinct serotypes, compared in vivo the exotoxin A neutralizing activity of PS-IGIV with that of an IGIV of similar formulation, and investigated therapy of established Pseudomonas burn wound sepsis with combinations of PS-IGIV and orally administered ciprofloxacin. The combination therapy was found to enhance the effectiveness of ciprofloxacin against P. aeruginosa and S. aureus.

Pseudomonas Immune Globulin, Intravenous (PS-IGIV) is currently in clinical trials in the US and Europe. PS-IGIV is prepared from plasma of donors that have naturally high levels of IgG antibody to lipopolysaccharide antigens of P. aeruginosa as set forth in U.S. Pat. No. 4,587,121. It contains 5% IgG in 10% maltose and is prepared for intravenous infusion by a low pH process. The prophylactic activity of PS-IGIV in a burned mouse model was evaluated against 18 clinical isolates of P. aeruginosa representing 17 distinct International Antigenic Typing System serotypes. In burned mice challenged with approximately 10 to 100 mean lethal doses ($LD_{50}$) the mean protective dose ($PD_{50}$) against the 18 strains ranged from less than 56 to 252 mg IgG/kg. In part, PS-IGIV protection may have resulted from neutralization of exotoxin A. In PS-IGIV treated mice challenged with 4 $LD_{50}$ of exotoxin A, serum levels of aspartate and alanine aminotransferase were several-fold lower than those of mice treated with conventional IgG concentrates.

Ciprofloxacin is a recently developed quinoline carboxylic acid derivative that is well absorbed when given orally and attains high concentrations in extravascular fluid. For treatment of established burn wound sepsis, therapy with ciprofloxacin and PS-IGIV was delayed until 16 hours after challenge with three strains of P. aeruginosa. Oral dosages of ciprofloxacin were selected (2.5 to 15 mg/kg/dose × 6) that afforded survival to approximately 50% of ciprofloxacin treated mice. PS-IGIV was given once by the intraperitoneal route. Overall survival was 1.7% (N=60) in albumin treated control mice. Survival in mice treated with ciprofloxacin or PS-IGIV alone was 46.7% (N=60) and 13.3% (N=60) respectively. Survival in mice treated with both agents was 80.0% (N=60). These results suggest that combination therapy of life threatening Pseudomonas burn wound sepsis with ciprofloxacin and PS-IGIV may have clinical utility.

MATERIALS AND METHODS

Bacteria and inocula preparation

The 18 strains of P. aeruginosa listed in Table 1 are blood isolates obtained from the laboratory of Dr. A. E. Brown, Memorial Sloan-Kettering Cancer Center. The isolates were serotyped by live antigen agglutination using 17 monospecific International Antigen Typing Schema (IATS) antisera according to instructions of the manufacturer (Difco Laboratories, Detroit, MI). Very weak agglutination reactions were considered negative. Fisher-Devlin-Gnabasik (FDG) immunotype 1, strain 1369 was obtained from Dr. J. A. Bass, Shriners Hospitals for Crippled Children, Galveston, TX. FDG 2, ATCC 27313, and FDG 6, ATCC 27317, were obtained from the American Type Culture Collection. Inocula for in vivo studies were prepared as previously described.

Animals

Female Swiss-Webster mice, CrL:CFW(SW)BR weighing 22-26 g were obtained from Charles River, Wilmington, MA. For each study mice were matched by age and weight. Animals were housed 10 per cage and freely given water and mouse chow.

IgG preparations

Donors identified by an enzyme linked immunosorbent assay as having naturally high levels of IgG antibody to LPS antigens of *P. aeruginosa* were the source of plasma for preparation of PS-IGIV. All plasma used for production of PS-IGIV and IGIV are currently determined to be negative for HTLV-III antibodies by an FDA approved serologic assay. Pooled plasma was fractionated by the Cohn-Oncley process. PS-IGIV and IGIV were prepared for intravenous infusion by a low pH process (U.S. Pat. No. 4,396,608; Aug. 2, 1983). Both IgG preparations contain $5\pm1\%$ protein of which no less than 90% has the electrophoretic mobility of IgG. The IgG preparations are stabilized with $10\pm2\%$ maltose and have a pH of $4.25\pm0.25$. The buffer capacity is 0.3 mEq/g of protein and the calculated osmolarity is 292 mOs/L.

PS-IGIV prophylaxis studies

Mice were given a 10% body surface area, full thickness dorsal burn with a gas flame as previously described. The mean lethal dose ($LD_{50}$) of the 18 clinical isolates was estimated by injection of $10^2$, $10^4$, or $10^6$ colony forming units (cfu) in 0.5 ml saline into the burn sites of 5 mice per dose. For prophylaxis studies, a 0.25 vol. of PS-IGIV lot P5226 diluted in 5% human serum albumin (HSA) was given by the intraperitoneal route 3 hours before burn and challenge. PS-IGIV was administered to 10 mice each at 0, 56, 167 or 500 mg/kg body weight. Preliminary studies indicated that by 3 hours after PS-IGIV administration, human IgG levels in the plasma of mice were the same whether PS-IGIV was given via a tail vein or by the intraperitoneal route. Animals were observed for 15 days following challenge.

Therapy of established Pseudomonas burn wound sepsis

Burned mice were challenged with FDG 1-1369, FDG 2 ATCC 27313 or FDG 6 ATCC 27318 at inocula levels indicated in Table 2. Ciprofloxacin was delivered into the stomach in 0.1 ml volume via a 23 gauge animal feeding needle at 16, 24, 40, 48, 64 and 72 hours after challenge. Control animals received 0.1 ml of water. PS-IGIV lot P5226 or an equivalent volume of 5% HSA was administered by the intraperitoneal route once at 16 hours after challenge. Dosages of ciprofloxacin and PS-IGIV are described in Table 2.

Therapy of established polymicrobial burn wound sepsis

Burned mice were challenged in the wound site with mixtures of *S. aureus* and *P. aeruginosa*. Ciprofloxacin batch 907337 was a gift of Dr. B. Painter, Miles Laboratories, Inc., West Haven, CT. The drug was solubilized in water and administered in a 0.1 ml volume into the stomach through a 23 gauge animal feeding needle at 16, 24, 40, 48, 64 and 72 hours after challenge. Control mice received 0.1 ml water orally. PS-IGIV or HSA was administered by the ip route once 16 hours after challenge. Animals were observed for 15 days.

Statistics $PD_{50}$ of immunoglobulin and ciprofloxacin was determined by the Finney probit test. PS-IGIV vs IGIV vs Pentaglobin ® prophylaxis was evaluated by multiple logistic regression (SAS ® Users Group International. SOGI Supplemental Library users Guide, Version 5 Edition). Tables 2A, 2B, and 2C reflect the data and results from the therapy of polymicrobial infections.

Exotoxin A studies

Exotoxin A derived from *P. aeruginosa* PA103 was a gift of Mr. M. Lostrom, Genetic Systems Corp. Seattle, WA. The toxin was prepared by described methods (12). When injected by the intraperitoneal route into 24 to 26 g normal mice, 1.5 µl of the toxin concentrate contained one $LD_{50}$. For neutralization studies, PS-IGIV and IGIV were injected by the intraperitoneal route 3 hours before injection of 2 or 4 $LD_{50}$ of exotoxin A. Mice were observed for 5 days. To evaluate exotoxin A-medicated tissue damage, mice surviving 18 hours after exotoxin A challenge were bled from a tail vein, and serum levels of aspartate aminotransferase (AST) and alanine aminotransferase (ALT) were determined by UV spectroscopy (Procedure No. 55-UV, Sigma Diagnostics, St. Louis, MO).

RESULTS

Antibody to LPS antigens in PS-IGIV

PS-IGIV lot P5226 employed in these studies was compared with 14 lots of IGIV for antibody levels to LPS antigens representing the 7 FDG immunotypes of *P. aeruginosa*. By ELISA PS-IGIV contained from 4.15-fold (FDG 7) to 11.72 fold (FDG 4) more antibody to LPS than conventional IGIV (Table 1).

TABLE 1

Enzyme-linked immunoassay of IgG levels to lipopolysaccharide in Pseudomonas immune globulin, intravenous (PS-IGIV) and conventional immune globulin, intravenous (IGIV)

| Immunotype | Titer[a] PS-IGIV (P5226) | IGIV[b] | PS-IGIV IGIV |
|---|---|---|---|
| 1 | 11,253 | 2,324 ± 369 | 4.84 |
| 2 | 21,340 | 4,315 ± 1,115 | 4.95 |
| 3 | 2,780 | 462 ± 97 | 6.02 |
| 4 | 22,029 | 1,879 ± 389 | 11.72 |
| 5 | 3,149 | 335 ± 98 | 9.40 |
| 6 | 12,671 | 1,806 ± 307 | 7.02 |
| 7 | 3,434 | 828 ± 242 | 4.15 |
| Mean | 10,951 | 1,707 | 6.42 |

[a]Titer determined by linear regression of absorbance of two-fold dilutions of 5% IgG.
[b]Mean titers ± SD of 14 lots of IGIV.

Prophylaxis in experimental infection

Virulence of the 18 clinical isolates of *P. aeruginosa* in the burned mouse model varied greatly. The $LD_{50}$ of the strains ranged from $<10^2$ to approximately $10^6$ cfu (Table 2). Half of the 18 strains agglutinated in two or more IATS antisera. Polyagglutinating isolates did not tend to be less virulent than isolates agglutinating in only one IATS antiserum. Overall, 158 of 180 mice treated only with HSA died. The mean protective dose ($PD_{50}$) of PS-IGIV ranges from $<56$ to 252 mg IgG/kg body weight. PS-IGIV afforded better protection to mice challenged with *P. aeruginosa* strains expressing one or more FDG LPS antigens. Protection was poorer against the 3 strains expressing only IATS LPS antigens. Clinical isolates expressing IATS 16 and 17 LPS antigens were not available for study.

TABLE

PS-IGIV prophylaxis of Pseudomonas burn wound sepsis: activity against 18 clinical isolates

| Strain | Serotype | Inoculum (cfu) | Cumulative mortality. No. dead/total PS-IGIV mg/kg body weight[a] | | | | Mean[b] protective dose (mg/IgG/kg) |
|---|---|---|---|---|---|---|---|
| | | | 0 | 56 | 167 | 500 | |
| 44966 | FDG 1[c] | $1.8 \times 10^4$ | 8/10 (4.6 ± 1.8)[d] | 1/10 (7) | 0/10 | 1/10 (8) | 38.8 |
| 56757 | FDG 1 | $8.0 \times 10^1$ | 10/10 (6.6 ± 5.0) | 2/10 5.5 ± 3.5) | 2/10 (3 ±0) | 2/10 (6.5 ± 0.7) | 63.0 |
| 73404-2 | FDG 1 (IATS 3) | $1.5 \times 10^2$ | 10/10 (2.4 ± 0.7) | 0/10 | 0/10 | 2/10 (4 ± 0) | 38.8 |
| 69840 | FDG 1, 5 (IATS 14) | $3.2 \times 10^3$ | 10/10 (2.2 ± 0.4) | 5/10 (3.6 ± 1.5) | 4/10 (7.3 ± 4.7) | 0/10 | 84.0 |
| 781 | FDG 2 (IATS 14) | $1.5 \times 10^6$ | 8/10 (4.9 ± 2.2) | 4/10 (7.5 ± 1.3) | 1/10 (7) | 2/10 (2.5 ± 0.7) | 72.0 |
| 30003 | FDG 2 | $8.5 \times 10^4$ | 10/10 (3.0 ± 1.8) | 2/10 (3.0 ± 1.4) | 5/10 (7.2 ± 1.9) | 0/10 | 72.0 |
| 27363 | FDG 2 | $1.4 \times 10^3$ | 8/10 (3.5 ± 0.9) | 2/10 (6.5 ± 3.5) | 2/10 (8.0 ± 4.2) | 3/10 (4.3 ± 3.1) | 72.0 |
| 44619 | FDG 3 (IATS 4) | $1.5 \times 10^3$ | 9/10 (3.3 ± 0.9) | 0/10 | 0/10 | 0/10 | $<56.0$ |
| 46158 | FDG 3, 7 | $1.7 \times 10^2$ | 8/10 (2.3 ± 0.7) | 3/10 (4.0 ± 3.5) | 3/10 (4.0 ± 2.6) | 0/10 | 63.0 |
| 77671 | FDG 4 | $4.8 \times 10^6$ | 6/10 (5.7 ± 3.1) | 0/10 | 0/10 | 0/10 | $<56.0$ |
| 63399-1 | FDG 4, 5 (IATS 3) | $1.3 \times 10^3$ | 9/10 (3.4 ± 1.2) | 5/10 (2.6 ± 1.3) | 1/10 (2) | 1/9 (2) | 72.0 |
| 64459 | FDG 5 (IATS 12, 13, 15) | $1.4 \times 10^4$ | 10/10 (2.7 ± 1.3) | 9/10 (3.4 ± 0.9) | 1/10 (7) | 0/10 | 100.0 |
| 49288 | FDG 6 | $2.6 \times 10^2$ | 7/10 (3.9 ± 0.7) | 4/10 (3.8 ± 0.5) | 3/10 (5.0 ± 1.0) | 1/10 (8) | 84.0 |
| 59371 | FDG 6, 7 | $1.1 \times 10^3$ | 9/10 (2.3 ± 1.1) | 1/10 (2) (3.6 ± 1.5) | 0/10 | 2/10 (4.0 ± 0) | 45.8 |
| 63826 | FDG 7 | $1.5 \times 10^2$ | 10/10 (2.4 ± 0.7) | 1/9 (5) | 0/9 | 0/10 | 36.0 |
| 72269 | IATS 3 | $1.5 \times 10^5$ | 7/10 (2.6 ± 0.8) | 3/10 (4.3 ± 2.1) | 3/10 (4.0 ± 1.0) | 84.0 (4.3 ± 0.6) | |
| 76375-2 | IATS 3, 12 | $7.8 \times 10^5$ | 9/10 (3.8 ± 0.8) | 6/10 (6.3 ± 2.7) | 4/10 (5.0 ± 1.8) | 168.0 (8.0 ± 1.4) | |
| 69375 | IATS 4 | $4.0 \times 10^6$ | 10/10 (2.9 ± 1.9) | 8/10 (4.9 ± 1.9) | 4/10 (7.5 ± 4.8) | 5/10 (3.8 ± 2.0) | 252.0 |
| | | | 158/180 (87.8%) | 56/179 (31.3%) | 35/179 (19.6%) | 26/179 (14.5%) | |

[a] PS-IGIV given by the intraperitoneal route 3 hours before burn and challenge.
[b] Mean protective dose determined by Finney probit test.
[c] Fisher-Devlin-Gnabasik immunotypes 1 through 7 correspond to IATS serotypes 6, 11, 2, 1, 10 (7, 8) and 5 respectively.
[d] Mean day of death ± SD.

TABLE 2A

Mortality in polymicrobial *Staphylococcus aureus* and *Pseudomonas aeruginosa* burn wound sepsis.

| P. aeruginosa Immunotype-strain | P. aeruginosa cfu in burn site | S. aureus in burn site | | No. S. aereus in burn site | |
|---|---|---|---|---|---|
| 1-1369 | 0 | 1/10[a] | (11) | 0/10[b] | |
| 1-1369 | 430 | 10/10 | (2 ± 0) | 6/10 | (3.2 ± 0.4) |
| 5-ATCC 27316 | 0 | 1/10[c] | (2) | 0/10[b] | |
| 5-ATCC 27316 | 40 | 9/10 | (2.1 ± 0.3) | 3/10 | (3.7 ± 0.6) |

[a] 75 cfu of *S. aureus* ATCC 14514 injected into burn site.
[b] Unchallenged burned trauma controls.
[c] 113 cfu of *S. aureus* ATTC 14514 injected into burn site.

TABLE 2B

Immunoglobulin prophylaxis against *Pseudomonas aeruginosa* and *S. aureus* burn wound sepsis

| P. aeurginosa Immunotype-strain (cfu) | Ig mg/kg | No. dead/total (Mean day of death ± SD) | | |
|---|---|---|---|---|
| | | PS-IGIV | IGIV | Pentaglobin ® |
| FDG 1-1369 | 0 | 7/10 (2.0 ± 0) | 7/10 (2.0 ± 0) | 7/10 (2.0 ± 0) |
| ($5.3 \times 10^2$) | 3 | 5/10 (2.8 ± 1.1) | 6/10 (2.3 ± 0.5) | 7/10 (2.3 ± 0.5) |
| ATCC 14154 | 10 | 1/10 (2) | 6/10 (2.2 ± 0.4) | 7/10 (3.3 ± 2.2) |
| ($1.1 \times 10^2$) | 30 | 0/10 | 3/10 (3.0 ± 0) | 3/10 (4.7 ± 1.9) |
| FDG 5-ATCC 27316 | 0 | 7/10 (2.1 ± 0.4) | 7/10 (2.1 ± 0.4) | 8/10 (4.3 ± 2.9) |
| ($5.5 \times 10^1$) + *S. aureus* | 11 | 8/10 (2.5 ± 0.5) | 9/10 (2.6 ± 0.8) | 9/10 (2.3 ± 0.5) |
| ATCC 14154 | 33 | 3/10 (2.5 ± 0.7) | 6/10 (2.3 ± 0.5) | 4/10 (2.0 ± 0.7) |
| ($8.5 \times 10^1$) | 100 | 1/10 (2) | 1/10 (3) | 2/10 (2.0 ± 0) |

TABLE 2C

Summary of immunoglobulin prophylaxis results for polymicrobial infections

| Organism-strain | Protective dose 50%[a] mg/kg (95% confidence limits) | | | Difference in immunoglobulin protection[b] | | |
|---|---|---|---|---|---|---|
| | PS-IGIV | IGIV | Pentaglobin ® | PS-IGIV Pentaglobin ® | IGIV vs Pentaglobin ® | PS-IGIV vs IGIV |
| *P. aeruginosa* FDG 1 1369 plus *S. aureus* ATCC 14154 | 4.8 (0.05-9.6) | 25.9 (No limits) | >10; <30[c] | .003 | NS | .012 |
| *P. aeruginosa* FDG 5 ATCC 27316 plus *S. aureus* ATCC 14154 | 37.1 (11.3-81.3) | 57.4 (NLL[e]-117.2) | 61.7 (14.6-256.3) | NS[d] | NS | NS |

[a]Protective dose 50% determined by Finney probit test.
[b]P difference determined by logistic regression.
[c]Protective dose 50% not calculable.
[d]NS is not significant. P > .05.
[e]NLL is no calculable lower confidence limit.

Therapy of established polymicrobial burn wound sepsis

Given alone, *S. aureus* ATCC 14154 alone was not lethal when injected into the wound site of burned mice. Preliminary studies indicated that the $LD_{50}$ of *S. aureus* was $>10^8$ cfu in burned mice. Inocula of *P. aeruginosa* FDG1-1369 and FDG 5 ATCC 27316 killed 60% and 30%, respectfively, of challenged animals in the same model (Table 2A). When *S. aureus* was added to the FDG 1 or FDG 5 inoculum, mortality increased to 100 and 90% respectively, and the mean time to death decreased by 1 day for each immunotype (Table 2A). Quantitative cultures of the burn wound site of several mice 16 hours after challenge indicated that *S. aureus* and *P. aeurginosa* (both immunotypes) were present in the burn site at $\geq 7 \times 10^7$ cfu/g of tissue. When started 16 hours after challenge, ciprofloxacin alone was effective therapy for FDG 1 and FDG 5 polymicrobial sepsis if administered orally at 10 mg/kg/dose (Table 3A). Overall, the $PD_{50}$ of ciprofloxacin was 5.0 mg/kg/dose. When ciprofloxacin was given orally to mice that had received either 100 or 500 mg PS-IGIV/kg body weight, the $PD_{50}$ of ciprofloxacin was decreased from 5.0 mg/kg to 1.5 and 0.11 mg/kg respectively. At 500 mg/kg, PS-IGIV given alone was effective therapy in mice challenged with *P. aeruginosa* immunotype 1 and *S. aureus*.

Therapy of established infection

Therapy of mice challenged with FDG immunotypes 1, 2 or 6 was delayed until 16 hours after subcutaneous injection of inocula into the burn site. At this time quantitative culture of the burn site always indicated $>10^7$ cfu of *P. aeruginosa*/g of tissue. Burn wound sepsis was highly lethal in mice challenged with FDG 1, 2 or 6. Overall, only 1 to 60 HSA treated control mice survived to the 15th day after challenge (Table 3). Dosages of ciprofloxacin that had been predetermined to afford approximately 50% survival to infected burned mice afforded from 40 (FDG 2) to 55% survival (FDG 6) in this study. The $PD_{50}$ of ciprofloxacin ranged from approximately 2.5 to 15.0 mg/kg/dose. This 6-fold range in the $PD_{50}$ of ciprofloxacin correlated poorly with the in vitro minimum inhibitory concentration (MIC) of ciprofloxacin for these three strains. As determined by two-fold dilution of ciprofloxacin in the Muller-Hinton agar, the MIC of ciprofloxacin for the challenge strains of FDG 1, 2 and 6 was 0.125, 0.250 and 0.250 μg ciprofloxacin/ml, respectively. PS-IGIV therapy alone was protective against FDG 1. Against FDG 2 and 6 PS-IGIV therapy alone did not increase survival; however, a small increase in mean time to death was noted. In each of the three experimental infections, combination therapy with PS-IGIV and ciprofloxacin was superior to single agent therapy. Overall survival in mice treated only with ciprofloxacin was 46.7% (28 of 60). When oral ciprofloxacin therapy was combined with a single dose of PS-IGIV, survival rose to 80% (48 of 60).

TABLE 3
Therapy of established Pseudomonas burn wound sepsis with PS-IGIV and oral ciprofloxacin.

| Therapy | Cumulative mortality. No dead/total P. aeruginosa immunotype (LD$_{50}$ injected in burn site) | | |
|---|---|---|---|
| | 1 (600 LD$_{50}$) | 2 (40 LD$_{50}$) | 6 (50 LD$_{50}$) |
| HSA only | 19/20[a] (2.0 ± 0.6) | 20/20 (1.7 ± 0.7) | 20/20 (2.0 ± 0.6) |
| Cioprofloxacin[b] + HSA | 11/20[d] (5.0 ± 4.0) | 12/20[d] (4.4 ± 4.2) | 9/20[e] (3.3 ± 2.0) |
| PS-IGIV only[c] | 12/20[d] (3.3 ± 2.1) | 20/20 (3.6 ± 2.7) | 20/20 (2.4 ± 1.3) |
| Ciprofloxacin + PS-IGIV | 7/20[e] (6.3 ± 2.0) | 4/20[e] (3.3 ± 4.5) | 1/20[e] (5) |

[a]Mean day of death ± SD.
[b]Mice challenged with immunotypes 1, 2 or 6 received 2.5, 5.0 or 15.0 mg ciprofloxacin/kg/dose respectively.
[c]Mice challenged with immunotypes 1, 2 or 6 receive 100, 100 or 250 mg PS-IGIV or HSA/kg respectively.
[d]P < .05, chi-square with Yates correction.
[e]P < .001.

TABLE 3A
Therapy of *Pseudomonas aeruginosa* and *Staphylococcus aureus* mixed burn wound sepsis with Pseudomonas IGIV and oral ciprofloxacin

| PS-IGIV[a] mg/kg | Ciprofloxacin[a] mg/kg/dose | No. dead total (Mean day to death ± SD) | | | |
|---|---|---|---|---|---|
| | | Immunotype 1[b] | P | Immunotype 5 | P |
| 0 | 0 | 10/10 (2.0 ± 0) | | 9/10 (2.1 ± 0.3) | |
| | 2.5 | 6/10 (2.3 ± 0.5) | NS[d] | 9/10 (3.2 ± 1.8) | NS |
| | 5.0 | 6/10 (3.3 ± 2.5) | NS | 6.10 ((6.0 ± 4.5) | NS |
| | 10.0 | 3.10 (3.0 ± 1.7) | <.05 | 1.10 (2) | <.05 |
| 100 | 0 | 7.10 (3.0 ± 0.8) | NS | 7.10 (2.2 ± 0.4) | NS |
| | 2.5 | 4/10 (3.0 ± 0.2) | <.05 | 10/10 (2.2 ± 0.4) | NS |
| | 5.0 | 2/10 (3.0 ± 0) | <.01 | 2/10 (2.5 ± 0.7) | <.05 |
| | 10.0 | 2/10 (2.0 ± 0) | <.01 | 2/10 (2.8 ± 0.4) | NS |
| 500 | 0 | 2/10 (2.0 ± 0) | <.01 | 6/10 (2.8 ± 0.4) | NS |
| | 2.5 | 5/10 (3.0 ± 1.7) | (.07) | 2/10 (3.5 ± 0.7) | <.05 |
| | 5.0 | 1.10 (3) | <.01 | 1/10 (6) | <.05 |
| | 10.0 | 1/10 (2) | <.01 | 1/10 (4) | <.05 |

TABLE 3A
Therapy of *Pseudomonas aeruginosa* and *Staphylococcus aureus* mixed burn wound sepsis with Pseudomonas IGIV and oral ciprofloxacin Summary (Immunotype 1 + 5)

| % Dead | Ciprofloxacin PD$_{50}$ mg/kg/dose (95% confidence limits) |
|---|---|
| 95 | 5.0 |
| 75 | (3.0–9.9) |
| 60 | |
| 20 | |
| 70 | 1.5 |
| 70 | (no limits) |
| 20 | |
| 20 | |
| 40 | 0.11 |
| 35 | (0.0–0.50) |
| 10 | |
| 10 | |

[a]PS-IGIV given i.p. 16 h after challenge. Ciprofloxacin given orally at 16, 24, 40, 48, 64 and 72 h.
[b]Burned mice challenged with 430 cfu of *P. aeruginosa* immunotype 1-1369 and 75 cfr *S. aureus* ATCC 14134.
[c]Burned mice challenged with 40 cfu of *P. aeruginosa* immunotype 5-ATCC 27316 and 113 cfu of *S. aureus* ATCC 14154.
[d]P is protection vs. untreated control group. NS is not significant; P > .05 by chi-square test.

Exotoxin A studies

Cumulative survival was 10% in control mice challenged with 2 or 4 LD$_{50}$ of exotoxin A (Table 4). No animal died after the fourth day of exotoxin A challenge. In mice challenged with 2 LD$_{50}$ of exotoxin A, both IgG preparations at 500 mg/kg body weight afforded ≧80% survival; however, the PD$_{50}$ of PS-IGIV was 2.3-fold lower than the PD$_{50}$ of IGIV. In mice challenged with 4 LD$_{50}$ of exotoxin A, PS-IGIV remained highly protective, and the PD$_{50}$ of PS-IGIV at 101 mg IgG/kg body weight was 5-fold lower than the PD$_{50}$ of IGIV.

TABLE 4
Lethality in exotoxin A-challenged mice treated with PS-IGIV or IGIV

| IgG, mg/kg | Cumulative mortality no. dead/total challenged with exotoxin A | | | |
|---|---|---|---|---|
| | IGIV treated | | PS-IGIV treated | |
| | 2LD$_{50}$ | 4LD$_{50}$ | 2LD$_{50}$ | 4LD$_{50}$ |
| 0 | 18/20 | 9/10 | 18/20 | 9/10 |
| 56 | 17/20 | 10/10 | 11/20[a] | 7/10 |
| 167 | 10/20[a] | 8/10 | 1/20[b] | 3/10[a] |
| 500 | 4/20[b] | 4/10 (P = .06) | 2/20[b] | 0/10[b] |
| PD$_{50c}$ | 168 mg/kg | 501 mg/kg | 72 mg/kg | 101 mg/kg |

[a]P < .05, chi-square with Yates correction.
[b]P < .001
[c]Mean protective dose by Finney probit test.

Challenge of HSA treated control mice with either 2 or 4 LD$_{50}$ of exotoxin A resulted in severe tissue damage indicated by grossly elevated serum levels of AST and ALT (Table 5). Enzyme levels in IGIV or PS-IGIV treated mice challenged with 2 LD$_{50}$ of exotoxin A were several-fold lower than those of HSA treated controls and only mildly elevated (about 2-fold) over AST and ALT levels of normal mice. In mice challenged with 4 LD$_{50}$ of exotoxin A, IGIV was unable to neutralize the toxin, for AST and ALT levels were not significantly lower than those of HSA treated controls, PS-IGIV, however, was protective. AST and ALT levels while considerably higher than normal were still significantly lower (P<0.5) than those of IGIV treated animals.

TABLE 5
Serum enzyme levels in exotoxin A challenged mice treated with PS-IGIV or IGIV

| Treatment[a] group | Exotoxin-A challenged | AST 2 LD$_{50}$ units/ml | AST 2 LD$_{50}$ Fold increase | AST 4 LD$_{50}$ units/ml | AST 4 LD$_{50}$ Fold increase | ALT 2 LD$_{50}$ units/ml | ALT 2 LD$_{50}$ Fold increase | ALT 4 LD$_{50}$ units/ml | ALT 4 LD$_{50}$ Fold increase |
|---|---|---|---|---|---|---|---|---|---|
| Albumin | No  | 54 ± 3[b]   | 1.0[c] | 64 ± 5       | 1.0  | 37 ± 2      | 1.0 | 34 ± 4        | 1.0  |
| Albumin | Yes | 524 ± 137   | 9.7    | 2737 ± 509   | 42.8 | 257 ± 77    | 6.9 | 638 ± 82      | 18.8 |
| IGIV    | Yes | 111 ± 44[d] | 2.1    | 2364 ± 2148  | 36.9 | 60 ± 21[d]  | 1.6 | 499 ± 396     | 14.7 |
| PS-IGIV | Yes | 107 ± 35[d] | 2.0    | 490 ± 272[d,e] | 7.7 | 60 ± 16[d]  | 1.6 | 159 ± 81[d,e] | 4.7  |

[a]Mice treated with 500 mg protein/kg body weight 3 h before exotoxin A or saline challenge.
[b]Mean serumenzyme level in international units ± SD. Serum of several mice each from each treatment group of 20 to 30 mice were combined into 3 to 4 pools per treatment group to have sufficient serum volume for AST and ALT assays.
[c]Mean increase compared to albumin-treated mice not challenged with exotoxin A.
[d]$P < .001$, IGIV or PS-IGIV treatment vs albumin (F test using analysis of variance with linear contrast).
[e]$P < .05$, PS-IGIV treatment vs IGIV treatment.

Nearly three decades ago it was reported that pooled human IgG is protective against experimental *P. aeruginosa* infection in normal and burned animals. Attempts in the 1960's to treat Pseudomonas infection with immune globulin were not very successful in part because of the limited amount of IgG that could be delivered by intramuscular injection of IgG concentrates. The development of IGIV formulations now allows infusion of 500 mg IgG/kg into burn patients without unwanted effects.

Passive protection studies using sera of animals immunized with LPS provide proof that IgG antibody to LPS is highly protective against *P. aeruginosa* in experimental infections. The protective activity of IGIV in experimental *P. aeruginosa* infection prompted this laboratory to consider that an IGIV enriched in antibodies to LPS might be more protective than IGIV prepared from plasma of random donors. Accordingly, several thousand donors were tested by ELISA for IgG titers to LPS antigens of the seven FDG immunotypes of *P. aeruginosa*. Approximately 5% of plasma donors had antibody titers ≧ 1:1,600 against FDG 1, 2, 4 and 6 LPS. Several hundred liters of plasma were obtained from ELISA tested donors, and PS-IGIV was produced. PS-IGIV is enriched from 4.84 to 11.72-fold in antibody to FDG 1, 2, 4 and 6 LPS (Table 1). Although not of intentional design, PS-IGIV is also enriched several-fold in IgG to FDG 3, 5 and 7. The present study indicates that PS-IGIV prophylaxis was protective in burned mice against all 18 clinical isolates examined. It should be noted that these 18 isolates were not preliminarily screened for sensitivity to IgG prophylaxis. Against 16 of these strains, the PD$_{50}$ of PS-IGIV was ≦100 mg IgG/kg body weight. PS-IGIV tended to be more protective against strains expressing FDG LPS antigens. Approximately 90% of *P. aeruginosa* strains isolated from serious infections fall within the FDG immunotype system.

Substantial clinical evidence suggests that the enzyme exotoxin A is an important virulence factor in the pathogenesis of *P. aeruginosa* infection. Approximately 80 to 90% of *P. aeruginosa* clinical isolates produce exotoxin A (Bjorn, M. J., M. L. Vasil, J. C. Sadoff, and B. H. Iglewski. 1977. Incidence of exotoxin production by Pseudomonas species. Infect. Immun. 16: 362–366 and Pollack, M., N. S. Taylor, and L. T. Callahan. 1977. Exotoxin production by clinical isolates of *P. aeruginosa*. Infect. Immun. 15: 776–780). Bacteremic patients infected with exotoxin A-producing strains have higher mortality rates than those infected with exotoxin A-negative strains (Cross, A. S., J. C. Sadoff, B. H. Iglewski, and P. A. Sokol. 1980. Evidence for the role of toxin A in the pathogenesis of infection with *P. aeruginosa* in humans. J. Infect. Dis. 142: 538–546). Recovery from serious *P. aeruginosa* infection correlates with serum neutralizing antibody to exotoxin A, whereas fatal infection is associated with minimal antibody response (Pollack, M., L. T. Callahan, and N. S. Taylor. 1976. Neutralizing antibody to *P. aeruginosa* exotoxin in human sera: evidence for in vivo toxin production during infections. Infec. Immun. 14: 942–947 and Pollack, M. and L. S. Young. 1979. Protective activities to exotoxin A and lipopolysaccharide at the onset of *P. aeruginosa* septicemia in man. J. Clin. Invest. 63: 276–286). Neutralizing IgG antibody to exotoxin A is found in sera of 40 to 50% of normal adults (Pollack, M., and N. S. Taylor. 1977. Serum antibody to *P. aeruginosa* exotoxin measured by a passive hemagglutination assay. J. Clin. Microbiol. 6: 58–61). Thus, it is not surprising that 27 lots of IGIV prepared from large pools of plasma by seven manufacturers contained similar levels of antibody to exotoxin A. Interestingly, a Pseudomonas hyperimmune IGIV prepared from donors immunized with a heptavalent LPS vaccine had an antitoxin titer comparable to the 27 normal IGIV preparations. The present report indicates that in addition to being enriched in IGG to LPS, PS-IGIV is also enriched in IgG to exotoxin A. A several-fold enrichment in antitoxin is suggested by the 5-fold lower PD$_{50}$ of PS-IGIV compared to IGIV in mice challenged with 4 LD$_{50}$ of exotoxin A (Table 4).

The rapid emergence of antibiotic resistance by *P. aeruginosa* and the relatively high toxicity of potent anti-Pseudomonas agents such as aminoglycosides encourage the continuing development and clinical evaluation of new antimicrobials. Ciprofloxacin is a relatively new fluoroquinoline derivative highly active against *P. aeruginosa* in vitro. In humans, ciprofloxacin has been given orally at dosages ranging from 5.2 to 8.7 mg/kg/dose twice daily for seven days. This oral regimen was safe and led to serum levels of the drug that were inhibitory against a large number of clincal isolates of *P. aeruginosa*. In this study, oral dosages of ciprofloxacin were empirically selected that protected approximately 50% of mice treated twice daily for three days (Table 3). These dosages ranged from 2.5 to 15 mg ciprofloxacin/kg/dose. Overall mortality in ciprofloxacin treated mice was 53.3%. This was reduced to 20% when PS-IGIV was added to the therapeutic regimen.

We also describe a rapidly lethal model of polymicrobial burn wound sepsis. For antimicrobial therapy of this infection, ciprofloxacin was given orally twice daily at dosages ranging from 2.5 to 10 mg/kg. When the protection data against two strains of *P. aeruginosa* were summarized, a $PD_{50}$ of 5.0 mg ciprofloxacin/kg was observed. This dosage is equivalent to 350 mg in a 70 kg man. At a dosage of 10 mg/kg, ciprofloxacin alone was significantly protective against the FDG 1 and 5 strains of *P. aeruginosa*. Combined therapy with ciprofloxacin and 100 or 500 mg PS-IGIV/kg markedly increased the potency of ciprofloxacin, as the $PD_{50}$ of ciprofloxacin was reduced from 5.0 to 1.5 and 0.11 mg/kg respectively. Because PS-IGIV is active against a variety of *P. aeruginosa* strains and because the immunoglobulin markedly enhanced the potency of ciprofloxacin and aminoglycosides, we conclude that PS-IGIV may be a useful adjuvant to antimicrobial therapy of serious *P. aeruginosa* infection in man.

Our observations that PS-IGIV is active in vivo against a variety of clinical isolates of multiple serotypes and that it is enriched in neutralizing antibody to exotoxin A in vivo suggest that PS-IGIV may be a useful adjunct to antibiotic therapy of life-threatening *P. aeruginosa* infections. This conclusion is supported by the observation that PS-IGIV enhances the potency of aminoglycosides (6) and ciprofloxacin in the therapy of established Pseudomonas burn wound sepsis.

Given the above disclosure, it is thought variations will occur to those skilled in the art. Accordingly, it is intended that the above example should be construed as illustrative and the scope of the invention should be limited only by the following claims.

What I claim is:

1. A method of increasing the survival rate in a mammal following the onset of burn wound sepsis, the method comprising orally administering to the mammal ciprofloxacin and parenterally administering to the mammal a Pseudomonas immune globulin having a titer of antibody to lopopolysaccharide antigens of Fisher immunotypes 1, 2, 4 and 6 of at least 1:6400.

2. The method of claim 1 wherein the titer of antibody to lipopolysaccharide antigens of *P. aeruginosa* of Fisher immunotypes 1–7 is sufficient to render the immune serum globulin effective in treating *P. aeruginosa* infections.

3. The method of claim 2 wherein the titer of functional antibody to exotoxin A in Pseudomonas immune globulin is five-fold greater than conventional immune globulin.

4. The method of claim 1 wherein the amount of ciprofloxacin is sufficient to attain concentrations of ciprofloxacin in extravascular fluid which are effective in treating *P. aeruginosa* infections.

5. The method of claim 1 wherein the burn wound sepsis is a result of *P. aeruginosa* infection.

6. The method of claim 5 wherein the burn wound sepsis further includes *Staphylococcus aureus*.

* * * * *

UNITED STATES PATENT AND TRADEMARK OFFICE
CERTIFICATE OF CORRECTION

PATENT NO. : 4,772,465

DATED : September 20, 1988

INVENTOR(S) : Michael S. Collins

It is certified that error appears in the above-identified patent and that said Letters Patent are hereby corrected as shown below:

In claim 1, line 6, "lopopolysaccharide" should be --lipopolysaccharide--.

Signed and Sealed this

Seventh Day of February, 1989

Attest:

DONALD J. QUIGG

Attesting Officer

Commissioner of Patents and Trademarks